United States Patent [19]

Luider et al.

[11] Patent Number: 4,935,407
[45] Date of Patent: Jun. 19, 1990

[54] THERMOCHEMILUMINESCENT CYCLODEXTRIN COMPLEXES

[75] Inventors: Theo M. Luider, Soplicht; Jan C. Hummelen, Mieune Botering; Johannes N. Koek, Schoolstraat; Hans Wynberg, Hartn, all of Netherlands

[73] Assignee: Akzo N.V., Arnhem, Netherlands

[21] Appl. No.: 99,865

[22] Filed: Sep. 22, 1987

[30] Foreign Application Priority Data

Sep. 23, 1986 [EP] European Pat. Off. ....... 86.201646.6

[51] Int. Cl.$^5$ ................ G01N 33/533; G01N 33/546; G01N 33/58; G07D 321/00
[52] U.S. Cl. ..................................... 514/58; 536/103; 436/544
[58] Field of Search ............ 536/103; 514/58; 436/544

[56] References Cited

U.S. PATENT DOCUMENTS

| | | | |
|---|---|---|---|
| 4,518,588 | 5/1985 | Szejtli et al. | 514/58 |
| 4,524,068 | 6/1985 | Szejtli et al. | 514/58 |
| 4,596,795 | 6/1986 | Pitha | 514/58 |
| 4,598,070 | 7/1986 | Ohwaki et al. | 514/58 |
| 4,608,366 | 8/1986 | Hasegawa et al. | 514/58 |
| 4,623,641 | 11/1986 | Szejtli et al. | 514/58 |
| 4,705,847 | 11/1987 | Hummelen et al. | 530/350 |
| 4,727,064 | 2/1988 | Pitha | 514/58 |
| 4,778,767 | 10/1988 | Hummelen et al. | 436/823 |
| 4,834,985 | 5/1989 | Elger et al. | 424/488 |

FOREIGN PATENT DOCUMENTS

WO83/03604 10/1983 PCT Int'l Appl. .

*Primary Examiner*—Ronald W. Griffin
*Attorney, Agent, or Firm*—Donna Bobrowicz

[57] ABSTRACT

Thermochemiluminescent complexes of an adamantylideneadamantane 1,2-dioxetane and a cyclodextrin are non-volatile at the temperatures used to excite the thermochemiluminescence. The complexes can be encapsulated in immunosensitized microcapsules, e.g., liposomes, to provide a labeled immunoreagent useful in immunoassay using thermochemiluminescent labeled immunoreagents.

9 Claims, 3 Drawing Sheets

THERMOCHEMILUMINESCENT CYCLODEXTRIN COMPLEXES

This invention relates to thermochemiluminescent cyclodextrin complexes and more particularly to thermochemiluminescent complexes of an adamantylideneadamantane 1,2-dioxetane and a cyclodextrin which are useful as labels in immunoassays.

Thermochemiluminescent compounds are those which upon heating, generally to a temperature above room temperature, undergo a chemical reaction which results in the emission of luminescence. Generally, compounds of this type undergo a thermally induced decomposition or rearrangement which yields a product in an electronic excited state capable of undergoing a radiative transition to a ground state with emission of luminescence.

A particular class of thermochemiluminescent compounds having utility in the field of immunoassay are the adamantylideneadamantane 1,2-dioxetanes, which undergo a thermochemiluminescent internal reaction upon heating to a temperature of about 240° C. In order to prepare a labeled immunoreagent capable of thermochemiluminescence, the adamantylideneadamantane 1,2-dioxetane nucleus is substituted with an organic radical which is capable of reacting with an immunoreagent, e.g., an antigen or antibody, to form a covalently linked labeled immunoreagent. The labeled immunoreagents can then be used in a conventional immunoassay. A thermochemiluminescent immunoassay is thereby possible wherein an immunoreagent labeled with a thermochemiluminescent substituent forms a complex with a complementary immunoreagent to yield a labeled immunocomplex which can be separated from the reagents, e.g., by precipitation or adsorption onto a solid support. The immunocomplex so formed can be quantitated by heating to stimulate the thermochemiluminescence of the label and measuring the amount of light emitted by the heated immunocomplex.

In an alternative embodiment, the thermochemiluminescent label may be encapsulated within a microcapsule, e.g., a liposome, which bears on its surface an immunoreagent. In an immunoreaction, the microcapsule, dispersed in an aqueous medium, becomes bound to a complementary immunoreagent in the medium to form an immunocomplex which is then separated from the medium by conventional means such as centrifugation, filtration or the like. The separated immunocomplex is then heated to excite the thermochemiluminescent compound and the amount of immunocomplex present is determined by measuring the amount of light emitted by the luminescent complex. The amount or concentration of unknown labeled immunocomplex is then determined in the conventional manner by comparison of the intensity of the luminescence with that of a series of standards of known amount or concentration.

However, a problem arises in thermochemiluminescent analyses using the adamantylideneadamantane 1,2-dioxetanes when the thermochemiluminescent label is not covalently bound to the immunoreagent, e.g., when the label is encapsulated in an immunosensitized microcapsule, e.g., a liposome. The adamantylideneadamantane 1,2-dioxetanes are appreciably volatile at the relatively high temperatures, e.g., 240° C., used to excite the thermochemiluminescence. When these compounds are covalently bound to a non-volatile immunoreagent, volatilization is prevented, but when the thermochemiluminescent compounds are merely contained in microcapsules, e.g., liposomes, they may be able to volatilize as the temperature is raised if the microcapsules themselves are ruptured upon heating. This is evidently a danger when microcapsules containing aqueous solutions are heated to temperatures above the boiling point of water, and is especially a problem with liposomes whose walls are merely fragile lipid membranes. The volatilized compounds are lost and, as a result, their luminescence is not detected and the measurement will be inaccurate.

Accordingly, a need has continued to exist for a means of increasing the accuracy of thermochemiluminescent immunoanalyses particularly when microcapsules are used as immunoreagents.

The problem of excessive volatility has now been solved by a method of thermochemiluminescent immunoanalysis using as the thermochemiluminescent label a novel complex of an adamantylideneadamantane 1,2-dioxetane with a cyclodextrin. According to the invention, a complex of a cyclodextrin and an adamantylideneadamantane 1,2-dioxetane is encapsulated in a microcapsule having on its surface an immunoreagent. The microcapsule so sensitized is then suspended in an aqueous solution and a complementary immunoreagent is mixed with the microcapsule suspension, whereby an immunocomplex of the sensitized microcapsule and complementary immunoreagent is formed. The immunocomplex is then separated from the solution and heated to a temperature at which the thermochemiluminescent reaction of the label is excited. The emitted light is quantitated and the amount of immunocomplex present is determined in the conventional way by comparison with a standard.

Accordingly, the present invention is concerned with a thermochemiluminescent complex of an adamantylideneadamantane 1,2-dioxetane and a cyclodextrin and a process for the preparation of said complex.

A further object of the invention is a method for immunoanalysis using this complex.

A further object is to provide a method of immunoassay using a thermochemiluminescent compound encapsulated in a microcapsule.

The Figures accompanying the present patent application show the following data:

Figure 1:
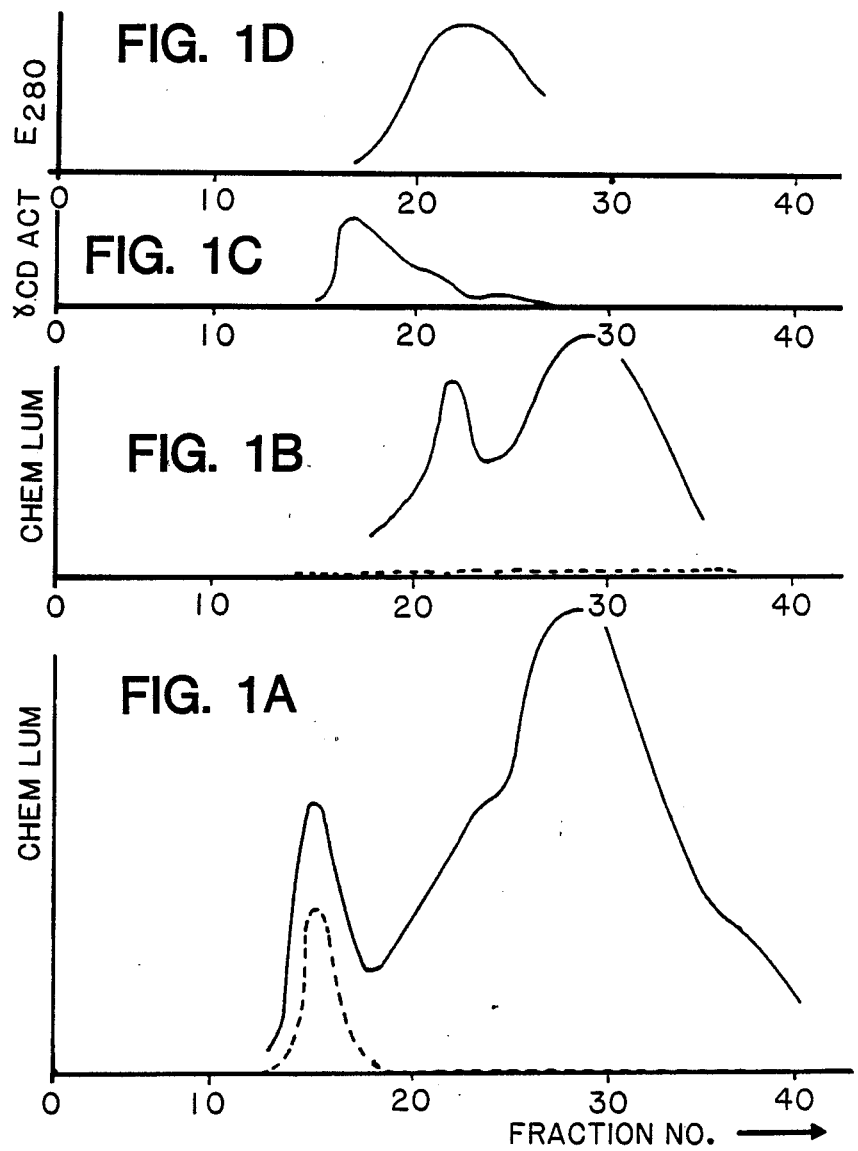
FIG. 1A shows the chromatogram of a thermochemiluminescent complex of the invention.
FIG. 1B shows the chromatogram of a solution containing only the thermochemiluminescent compound of Formula I.
FIG. 1C shows the chromatogram of a solution containing only gamma-cyclodextrin.
FIG. 1D shows the chromatogram of N-hydroxysuccinimide.

The thermochemiluminescent compounds of this invention are complexes of an adamantylideneadamantane 1,2-dioxetane and a cyclodextrine. Cyclodextrins are cyclic oligosaccharides obtained by the action of *Bacillus macerans* on starch to form homogeneous cyclic alpha-(1–4) linked D-glucopyranose units. Three principal cyclodextrins are known, identified as alpha-, beta- and gamma-cyclodextrin, and having rings comprising 6,7 and 8 glucose residues respectively. The preferred cyclodextrins for use in this invention are beta- and gamma-cyclodextrin. Gamma-cyclodextrin is the most preferred cyclodextrin.

In the present patent application the wording cyclodextrin is meant to include chemically modified cyclodextrin or cyclodextrins containing functional groups like the p-toluenesulfonyl-, azido-, halogen-, mesitylenesulfonyl-, perbenzoyl-, amino-, alkyl- or alkoxy groups. The cyclodextrin may be aminated, to e.g. cyclodextrin—$(OC_2H_4NH_2)_n$, —$(NH_2)_n$ or —$(NCH_3(CHO))_n$, be esterified, to e.g. cyclodextrin—$(ONO_2)_n$, —$(OSO_3H)_n$, —$(OPO_3H_2)_n$, —$(OCOC_6H_5)_n$ or —$(OCOCH_3)_n$, be etherified, to e.g. cyclodextrin—$(OCH_3)_n$, —$(OCH_2CO_2Na)_n$ or —$(OCH_2CHOHCH_2OH)_n$ or be methylated.

In the above formulas n may vary from 1 to the number of groups in the cyclodextrin molecule which are able to be substituted by the groups given above. These chemically modified cyclodextrins or these cyclodextrins comprising functional groups are known in the art and-as such-do not form part of the present invention.

The adamantylideneadamantane 1,2-dioxetanes useful according to this invention include compounds of the formula:

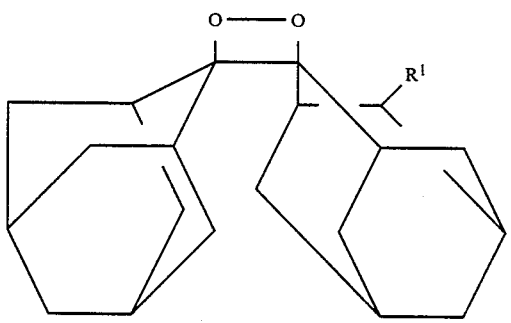

I wherein $R^1$ is selected from the group consisting of H, Cl, Br, F, I, OH, $NH_2$, $OR^2$ and $NHR^2$ wherein $R^2$ is an aliphatic organic radical containing no more than 20 carbon atoms. It will be evident to those skilled in the art that since the thermochemiluminescence of these molecules is due to the adamantylideneadamantane 1,2-dioxetane portion of the molecule, the exact nature of the substituent $R^1$ is not of great importance. It must not interfere with the thermochemiluminescent properties of the molecule, but, since the thermochemiluminescent center is somewhat remote from the substituent $R^1$, this condition is not difficult to satisfy. Accordingly, a wide range of substituents $R^1$ is possible. Besides the unsubstituted molecule wherein $R^1$ is H, $R^1$ may be a substituent such as halo, hydroxy or amino. Alternatively, $R^1$ may be an alkoxy or substituted amino group of the formula —$OR^2$ or —$NHR^2$ respectively, wherein $R^2$ is an aliphatic organic radical having a straight or branched chain of carbon atoms from $C_1$ to and including $C_{20}$. $R^1$ may also be an ester or amido group of the formula —$OR^2$ or —$NHR^2$ respectively, wherein $R^2$ is an acyl group containing up to 20 carbon atoms. Substituents $R^1$ containing functionally substituted groups $R^2$ are also useful, as well as those wherein one or more of the carbon atoms in the chain is replaced by an oxygen or nitrogen. In particular, omegasubstituted radicals may be used which have at the distal end of the radical a functional group capable of reacting with a protein. Such groups include mixed anhydrides, active esters, active carbonyl groups, and the like groups capable of reacting with the amino groups of proteins. Thus, the substituents $R^2$ may include $C_1$-$C_{20}$ aliphatic hydrocarbon groups such as methyl, ethyl, hexyl, decyl, stearyl, and arachidyl; aliphatic acid residues, such as acetyl, propanoyl, hexanoyl, lauroyl, stearoyl, and the like; aliphatic acid radicals having functional groups such as 3-hydroxy-propanoyl, 2-hydroxypropanoyl, and the like. The substituent $R^1$ must not interfere with the formation of the complex of the adamantylideneadamantane 1,2-dioxetane with cyclodextrin by reason of its steric or other properties. In particular, very bulky groups such as protein molecules and the like interfere with the formation of the complex and such groups are not preferred for substituents $R^1$. It has also been found that the substituted adamantylideneadamantane 1,2-dioxetanes wherein substituent $R^1$ is a relatively small group are better suited to form complexes with beta-cyclodextrin, whereas those compounds having larger substituents $R^1$ will only form useful complexes with gamma-cyclodextrin. In general the complexes with gamma-cyclodextrin are preferred.

Particularly preferred substituted adamantylideneadamantane 1,2-dioxetanes are those having the formulas:

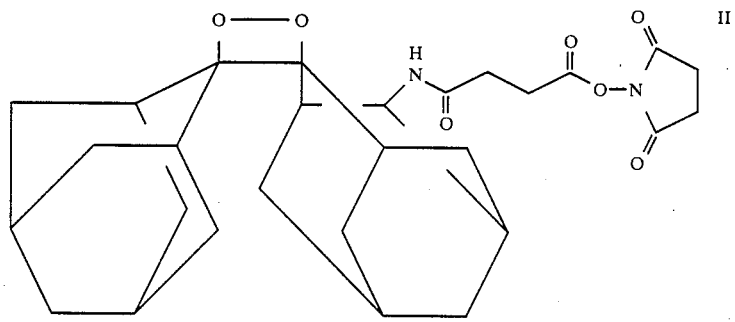

II

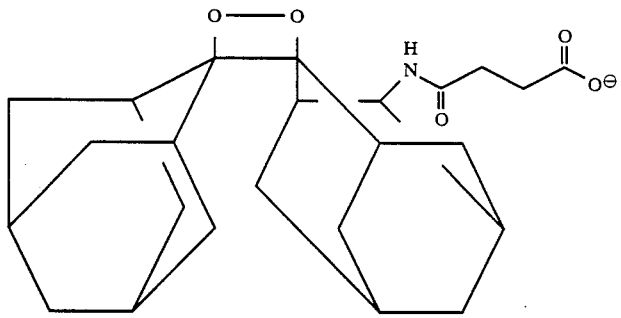

III

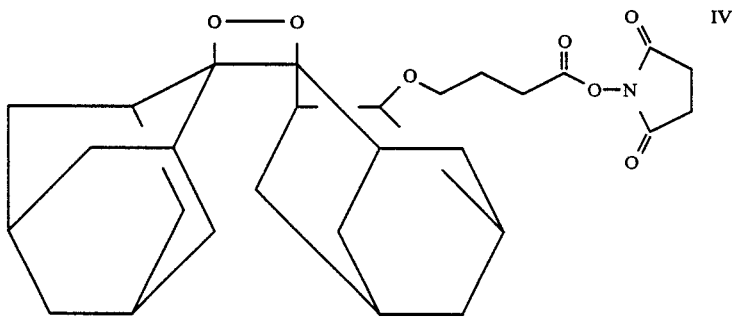

IV

The general preparation of the optionally substituted adamantylideneadamantane 1,2-dioxetanes used in preparing the thermochemiluminescent complexes of the invention is conventional and forms no part of this invention. Preparation of substituted adamantylideneadamantanes is disclosed in Meijer, E.W., et al., J. Org. Chem. 47, 2005 (1982). A general method for preparing the adamantylideneadamantane 1,2-dioxetanes is disclosed in Wieringa, J.H., et al., Tetrahedron Letters 1972, p. 169.

To prepare the thermochemiluminescent complexes of the invention the adamantylideneadamantane 1,2-dioxetane is contacted with the cyclodextrin in a suitable solvent. Since the compounds of formula I are relatively slightly soluble in water, while the cyclodextrins are soluble in water, the complexes are generally prepared by dissolving the compound of formula I in a water-miscible organic solvent and mixing this solution with an aqueous solution of the cyclodextrin. Suitable water-miscible organic solvents include dioxan, lower aliphatic alcohols such as ethanol, acetone, and 1,2-dimethoxyethane. A preferred water-miscible solvent for the adamantylideneadamantane 1,2-dioxetanes is dioxan.

The concentrations of thermochemiluminescent compound and of cyclodextrin should preferably be chosen to provide a large molar excess of cyclodextrin. The complexes are generally prepared by mixing a solution of a thermochemiluminescent compound in a water-miscible solvent and a solution of a cyclodextrin in water, although preparation by dissolving the thermochemiluminescent compound in an aqueous solution of cyclodextrin is not excluded. When the complexes are prepared by mixing solutions of the ingredients, the relative volumes used may vary widely. For example the complexes may be prepared by mixing approximately equal volumes of a solution of the thermochemiluminescent compound in a water-miscible solvent and an aqueous solution of cyclodextrin. Alternatively, the thermochemiluminescent compound may be dissolved in a relatively small amount of water-miscible solvent and this solution can be mixed with a relatively large amount of an aqueous solution of cyclodextrin. The concentrations of the solutions are chosen to provide at least an equimolar amount of cyclodextrin and thermochemiluminescent compound. However, in order to maximize the amount of thermochemiluminescent complex formed, it is preferred that the cyclodextrin be in substantial molar excess, e.g., a molar ratio of cyclodextrin to adamantylideneadamantane 1,2-dioxetane of 10:1 or greater, more preferably 20:1 or greater. The concentration of the adamantylideneadamantane 1,2-dioxetane in the water-miscible organic solvent may vary between wide ranges, e.g. from 0.001 mg/ml to 100 mg/ml, or even greater. A low concentration is used when the amount of solution of thermochemiluminescent compound is equal to or not much less than the volume of the aqueous cyclodextrin solution, while a high concentration is used when a relatively small amount of solution of the thermochemiluminescent compound is mixed with a substantially greater amount of aqueous cyclodextrin solution. The molar concentration of the cyclodextrin in the complex-forming solution should be substantially greater than that of the thermochemiluminescent compound. A concentration of 1 mg/ml of cyclodextrin in water is a convenient concentration and it may be even higher, up to a saturated aqueous solution. Typically, the adamantylideneadamantane 1,2-dioxetane is prepared as a solution in dioxane containing about 10 mg/ml (20 millimolar) and is mixed with about 20 volumes of an aqueous solution of cyclodextrin having a concentration of about 26 mg/ml (2o millimolar) to form the complex.

It is preferred to use the thermochemiluminescent complexes of this invention as reporter molecules in immunoassays using immunosensitized microcapsules, e.g., liposomes, as the immunoreagents. Such immunoassays are known and are disclosed, for example, in Uemura, K., et al., Biochemistry 11, 4085–4094 (1972), Kataoka, T., et al., Biochimica et Biophysica Acta 298, 158–179 (1973), Cole, U.S. Pat. No. 4,342,826, and Kakimi et al., U.S. Pat. No. 4,342,739. According to this invention, thermochemiluminescent complexes are encapsulated in immunosensitized microcapsules which are then used in the conventional manner to perform an immunoassay, e.g., by reaction with a complementary immunoreagent to produce precipitated immunocomplex, separation of the precipitate and quantitation of the separated immunocomplex. When the sensitized microcapsules contain a thermochemiluminescent complex of this invention, the separated precipitated liposome immunocomplex is placed in the heating chamber of a conventional thermochemiluminescence analyzer, heated to excite the chemiluminescence and the emitted luminescence is measured to obtain a quantitative estimate of the amount of immunocomplex.

The use of the thermochemiluminescent compounds of the invention in microcapsules has the advantage that it is possible to maintain a relatively high concentration of thermochemiluminescent compound and cyclodextrin within the liposome and thereby maintain the complex in the associated form. Since the association constant of the complex is about $10^4$–$10^5$, the complexes tend to dissociate at the extreme dilutions used in immunoassays. However, when the reagents are encapsulated in microcapsules the concentration of thermochemiluminescent reagent and cyclodextrin can be high enough to keep most of the material in the complexed form.

The microcapsules containing the thermochemiluminescent compounds of this invention may be prepared by conventional procedures such as coacervation, interfacial polymerization and the like. The formation of microcapsules is disclosed, for example, in Microencapsulation Processes and Applications, Jan E. Vandegger, Ed., Plenum press, 1974. Binding of immunoreagents, e.g., antigens or antibodies, to the surface of the microcapsules is disclosed, for example, in Kakimi et al., U.S. Pat. No. 4,342,739.

The following examples will illustrate the invention but are not intended to be limiting.

EXAMPLE 1

This example illustrates the preparation of a complex of gamma-cyclodextrin and an adamantylideneadamantane 1,2-dioxetane of the invention.

A solution, containing 5 milligrams of the compound of Formula II in 50 microliters of dioxane, was pipetted into one milliliter of an aqueous 20 mM borate buffer solution (pH 8.5), containing 2 milligrams of cyclodextrin. The molar ratio of the compound of Formula II to gamma-cyclodextrin was thus about 5:1. The complexes were then separated from the reagents by column chromatography on a column of cross-linked dextran (Sephadex LH60) 20 cm long×2.5 cm diameter, using a 20 mM borate buffer (pH 8.5). The chromatograms obtained are illustrated in FIG. 1, wherein the amount of material in each fraction of eluate collected was detected by properties appropriate to its chemical nature. FIG. 1A shows the chromatogram of the complex, while FIG. 1B shows the chromatogram of a solution containing only the thermochemiluminescent compound of Formula II. The materials were detected by their thermochemiluminescence. Measurements performed on an $Al_2O_3$ thin layer chromatography sheet (Merck) are given as a continuous line in FIGS. 1A and 1B, while measurements performed on Kapton 500M ®, manufactured by E.I. duPont de Nemours and Co., are given as a dotted line. FIG. 1C shows the chromatogram of a solution containing only gamma-cyclodextrin ($\gamma$-CD), wherein the amount of gamma-cyclodextrin in each fraction collected was determined by measuring the activity of the gamma-cyclodextrin by the method of Vikman (Vikman, M., I. Int. Symp. on Cyclodextrins, Budapest 1981, ed. J. Szejtli, pp. 69–74). FIG. 1D illustrates the chromatogram of N-hydroxysuccinimide, a hydrolysis product of the compound of Formula II, wherein the amount of N-hydroxysuccinimide in each fraction collected was determined by measuring the optical absorbance of the solution as a wavelength of 280 nm ($E_{280}$).

EXAMPLE 2

This example illustrates the excellent linearity and reproducibility obtainable with the thermochemiluminescent compounds of this invention and their lack of volatility at the temperatures used to excite the luminescence.

Figure 2:
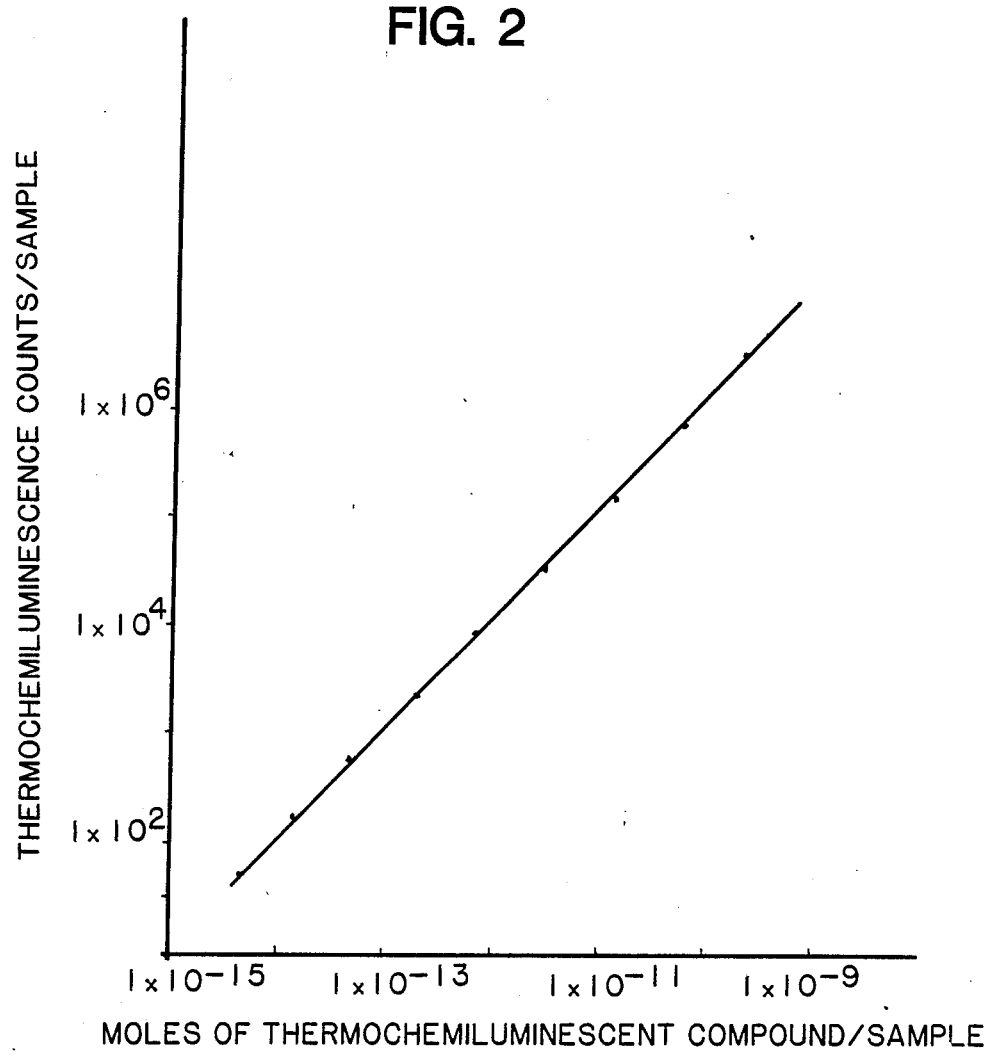
FIG. 2 shows a plot of chemiluminescence versus amount of the thermochemiluminescent complex of the invention (in a double logarithmic scale).

A thermochemiluminescence (TCL) complex was formed by the procedure of Example 1 and purified by chromatography over a cross-linked dextran gel (Sephadex LH60, 40–120 micron) column. A series of dilutions of the complex was prepared using 15 millimolar gamma-cyclodextrin solution as a diluent to prevent dissociation of the complexes. Samples of each of the dilutions were analyzed by a conventional thermochemiluminescent procedure. A drop of each sample was placed on a thin disk of a polyimide resin (Kapton 500M ®, manufactured by E.I. duPont de Nemours & Co.) and the sample so prepared was placed in the oven of a conventional thermochemiluminescence analyzer where it was heated to a temperature of 240° C. The intensity of the luminescence emitted by the heated sample is monitored by a photodetector, e.g., a multiplier phototube, whereby an electrical signal proportional to the intensity of the luminescence is generated. The signal is integrated over the heating time so that the integrated signal represents the total amount of luminescence emitted by the sample. The results are presented in FIG. 2 wherein the total number of counts representing quanta emitted (TCL counts/sample) is plotted against the number of moles of the compound of Formula II in the sample. Each point represents the average of six determinations. The coefficient of variation for each point was between 1.4% and 3.1%. (The coefficient of variation was corrected at low concentrations for counting statistics.) It can be seen from the plot that the linearity is excellent (correlation coefficient of linear regression r=0.9998), which indicates that none of the thermochemiluminescent compound is evaporating and being lost.

EXAMPLE 3

This example illustrates the preparation of liposomes containing the complex of adamantylideneadamantane 1,2-dioxetane and gamma-cyclodextrin.

The solution of Example 1 was encapsulated in liposomes by a conventional sonification procedure. Thirty-three micromoles of cholesterol and 33 micromoles of lecithin were dissolved in 2 milliliters of a mixed solvent of chloroform and methanol (volume ratio 1:1), and the solution was placed in a 50 milliliter round bottom flask and subjected to rotary evaporation until all solvent had been evaporated, leaving a coating of the solute on the walls of the flask. One milliliter of the solution prepared in Example 1 was added to the flask and the flask was subjected to ultrasonic vibration in a waterbath for one hour at 60° C. The resulting suspension of liposomes was subjected to exclusion column chromatography on a column of polyacrylamide gel beads (Sephacryl s300) in order to separate the liposomes from the solution containing unencapsulated reagents.

EXAMPLE 4

This example illustrates the thermochemiluminescence of the liposome-encapsulated complexes of this invention.

Figure 3:
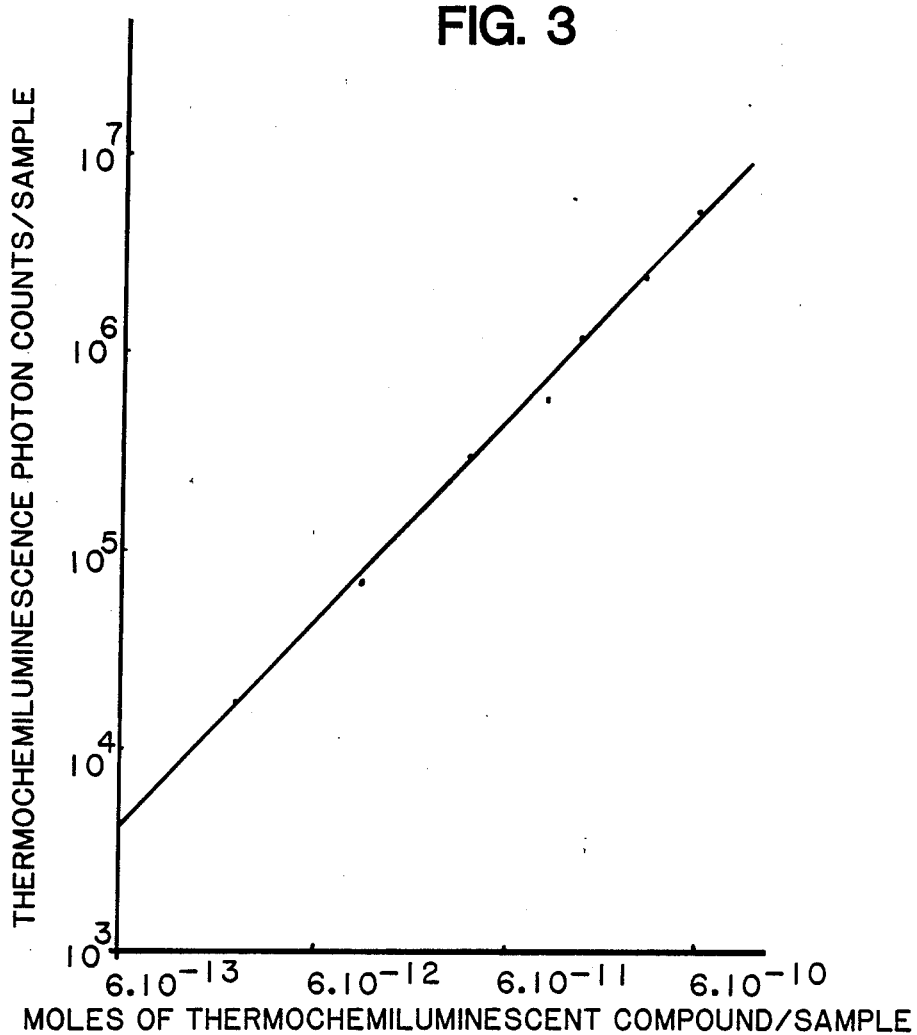
FIG. 3 shows a plot of chemiluminescence versus amount of thermochemiluminescent complex of the invention when the complex of the invention is encapsulated in a liposome (in a double logarithmic scale).

A dilution series of the liposomes prepared in Example 3 in a borate buffer (20 millimolar, pH 8.5) was then prepared. Small aliquots of each dilution were placed on Kapton ® disks and analyzed for their thermochemiluminescence as in Example 2, and the data were reduced and plotted by the same procedure. The resulting plot is shown in FIG. 3. The coefficient of variation for each point varied between 0.9% and 2.6%, while the correlation coefficient of linear regression r=0.996. These results again demonstrate the excellent reproducibility and linearity obtainable using the cyclodextrin complexes of this invention.

We claim:

1. A thermochemiluminescent complex comprising an adamantylideneadamantane 1,2-dioxetane and a cyclodextrin.

2. A thermochemiluminescent complex according to claim 1, wherein said cyclodextrin is gamma-cyclodextrin.

3. A thermochemiluminescent complex according to claim 1, wherein said adamantylideneadamantane 1,2-dioxetane has the formula:

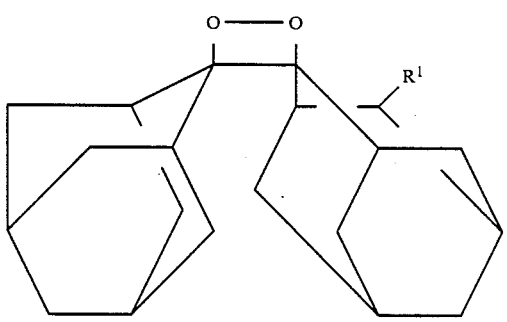

wherein $R^1$ is selected from the group consisting of H, Cl, Br, F, I, OH, $NH_2$, $OR^2$ and $NHR^2$, and wherein $R^2$ is an aliphatic organic radical containing no more than 20 carbon atoms.

4. A thermochemiluminescent complex according to claim 1, wherein said adamantylideneadamantane 1,2-dioxetane has the formula:

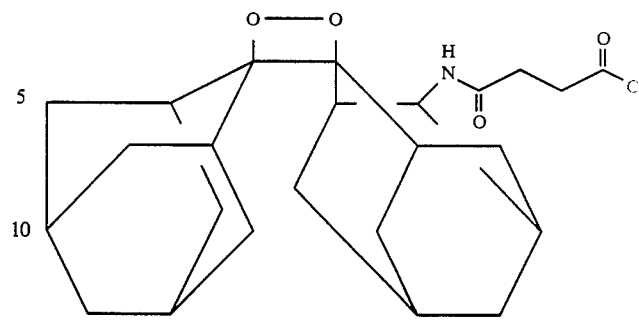

5. A thermochemiluminescent complex according to claim 4, wherein said cyclodextrin is gamma-cyclodextrin.

6. A method of immunoanalysis comprising encapsulating an aqueous solution comprising a thermochemiluminescent complex of an adamantylideneadamantane 1,2-dioxetane and a cyclodextrin within a microcapsule having an exterior surface, said exterior surface bearing an immunoreagent,
  contacting said microcapsule in aqueous suspension with an immunoreagent complementary to the immunoreagent on said exterior surface, whereby an immunocomplex is formed,
  separating said immunocomplex from said aqueous suspension,
  heating said separated immunocomplex to a temperature at which said complex undergoes a thermochemiluminescent reaction thereby emitting light, and
  determining the amount of light emitted in said thermochemiluminescent reaction.

7. The method according to claim 6, wherein said cyclodextrin is a gamma-cyclodextrin.

8. The method according to claim 6, wherein said thermochemiluminescent adamantylideneadamantane 1,2-dioxetane has the formula:

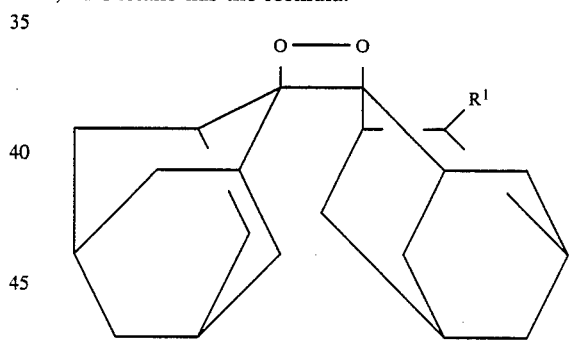

wherein $R^1$ is selected from the group consisting of H, Cl, Br, F, I, OH, $NH_2$, $OR^2$ and $NHR^2$, and wherein $R^2$ is an aliphatic organic radical containing no more than 20 carbon atoms.

9. The method according to claim 6, wherein said thermochemiluminescent adamantylideneadamantane 1,2-dioxetane has the formula:

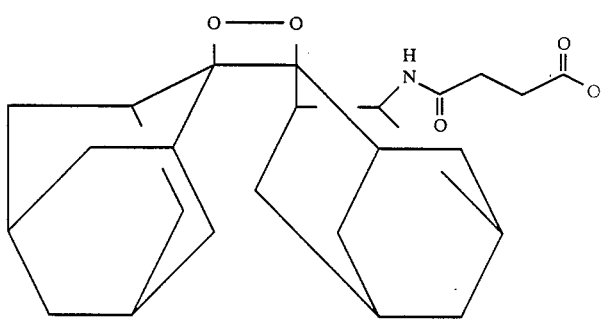

* * * * *